United States Patent [19]
Mann

[11] 4,324,251
[45] Apr. 13, 1982

[54] BATTERY MONITORING MEANS AND METHOD FOR AN IMPLANTABLE TISSUE STIMULATOR

[75] Inventor: Brian M. Mann, Northridge, Calif.

[73] Assignee: Pacesetter Systems, Inc., Sylmar, Calif.

[21] Appl. No.: 158,122

[22] Filed: Jun. 10, 1980

[51] Int. Cl.³ .............................................. A61N 1/36
[52] U.S. Cl. .............................................. 128/419 PT
[58] Field of Search .................... 128/419 PS, 419 PT

[56] References Cited
U.S. PATENT DOCUMENTS

| | | | |
|---|---|---|---|
| 3,837,348 | 9/1974 | Thaler | 128/419 PT |
| 4,082,097 | 4/1978 | Mann et al. | 128/419 PS |
| 4,231,027 | 10/1980 | Mann et al. | 128/419 PT |

*Primary Examiner*—William E. Kamm
*Attorney, Agent, or Firm*—John F. Buskirk

[57] ABSTRACT

A battery monitoring means for an implantable tissue stimulator in which a signal related to the internal impedance of an implanted battery is telemetered to an external receiving means. More specifically, the implanted battery is loaded by a varible load until current flowing through the battery lowers its output voltage until it has a predetermined relationship with respect to a reference voltage. The current flowing through the battery to achieve the predetermined relationship is directly related to the internal impedance of the battery. A voltage related to the value of this current is then telemetered to the external receiving means. In a specific embodiment, the variable load is a field effect transistor (FET) connected as a source follower. The impedance of the FET is controlled by the output of an operational amplifier having as inputs the reference voltage and a voltage related to the output voltage of the battery. The monitoring means operates in a closed-loop servo system manner until the two input voltages to the operational amplifier are equal. The other terminal of the battery is connected to a shunting resistor. Thus the voltage drop across the shunting resistor is related to the current drawn from, and the internal impedance of, the battery. This voltage is telemetered to the external receiving means.

20 Claims, 5 Drawing Figures

BATTERY MONITORING MEANS AND METHOD FOR AN IMPLANTABLE TISSUE STIMULATOR

FIELD OF THE INVENTION

The invention relates to battery monitoring systems for implantable tissue stimulators such as heart pacemakers and drug injection systems.

BACKGROUND OF THE INVENTION

Implantable tissue stimulators such as implantable pacemakers and implantable drug injection systems conventionally use an implanted battery as a power source. Although typical pacemaker batteries have a relatively long life, they do eventually require replacement. Such a replacement requires removal of the pacemaker and its subsequent reimplantation, thereby causing the patient to incur an additional, although minimal, risk. Consequently there has been a need to determine life remaining in an implanted battery so that it can be replaced at the optimal time, early replacement subjecting the patient to unnecessary risk and late replacement subjecting him to a possibility that his implanted device may fail. One technique for determining remaining battery life is described in U.S. Patent Application Ser. No. 16,200 filed Feb. 28, 1978. Basically, this technique loads the battery with a predetermined load and monitors the output voltage, this voltage indicating the internal impedance of the battery. Although this system has been generally satisfactory, it is independent upon the value of the loading impedance remaining known and constant. The present invention eliminates a need for loading the battery with predetermined load impedances by providing a closed loop servo means which depends for accuracy upon a reference voltage having a known value.

SUMMARY OF THE INVENTION

In an implantable living tissue stimulator powered by a battery having a positive terminal and a negative terminal, and having a telemetry means for transmitting and receiving signals related to the operation of the tissue stimulator, a battery monitoring means including means for drawing a loading current from the battery that results in the battery output voltage having a predetermined relationship with respect to a reference voltage, a means for generating a battery monitoring signal related to the loading current, and a means for providing the battery monitoring signal to the telemetry means. In addition, the invention provides a method for determining the internal impedance of an implanted battery including the steps of drawing a loading current from the battery that results in the battery output voltage having a predetermined relationship with respect to a reference voltage, the loading current being related to the internal impedance of the battery, generating a battery monitoring signal related to the loading current; and providing the battery monitoring signal to the telemetry means.

In a specific embodiment, the means for drawing a loading current from the battery is a field effect transistor (FET) connected as a source follower with its gate connected to the output of an operational amplifier having one input related to the output voltage of the battery, and another input being a reference voltage. The monitoring means operates in a closed loop servo manner so that the current through the FET is increased until the two input voltages to the operational amplifier are equal. At that time, the current flowing through the battery will be related to the internal impedance of the battery. A battery monitoring signal is generated related to the value of this current, and this signal is telemetered to an external receiving means. Thus the monitoring means above described provides an extremely accurate method of determining the internal impedance of a battery which is primarily dependent only upon the accuracy of the reference voltage.

BRIEF DESCRIPTION OF THE DRAWINGS

FIG. 5 is a qualitative representation of battery internal impedance as a function of the percent of battery life remaining.

DETAILED DESCRIPTION

Detailed illustrative embodiments of the invention disclosed herein exemplify the invention and are currently considered to be the best embodiments for such purposes. They are provided by way of illustration and not limitation of the invention. Various modifications thereof will occur to those skilled in the art, and such modifications are within the scope of the claims which define the present invention.

As previously explained, the invention provides a monitoring means for a battery implanted with an implantable tissue stimulator, the battery monitoring means providing a means for loading the battery so that its output voltage drops to a value that has a predetermined relationship with respect to a reference voltage. The current required to cause the battery output voltage to drop to this value is related to the internal impedance of the battery. This current, referred to hereinbelow as the loading current, is related to the internal impedance of the battery and thus to battery life remaining. Also disclosed is a means for generating a battery monitoring signal related to the loading current, this signal being provided to the implanted telemetry means for transmission to an external receiving means. In one exemplary embodiment, a field effect transistor (FET) connected as a source follower is connected to a positive output terminal of the battery. The FET is controlled by the output of an operational amplifier having as inputs a predetermined reference voltage and a voltage related to the actual output voltage of the battery. The operational amplifier is chosen to have an output voltage that causes the variable loading means to load the battery so that its output voltage has a predetermined relationship with respect to the reference voltage. At this time the current through the battery is determined. In the exemplary embodiment, the loading current flows through a shunting resistor which is connected between ground and the negative terminal of the battery. The voltage drop across the shunting resistor is then telemetered to the external receiving means. This voltage is directly related to the internal impedance of the battery, and thus provides an indication of battery life remaining.

Figure 1:
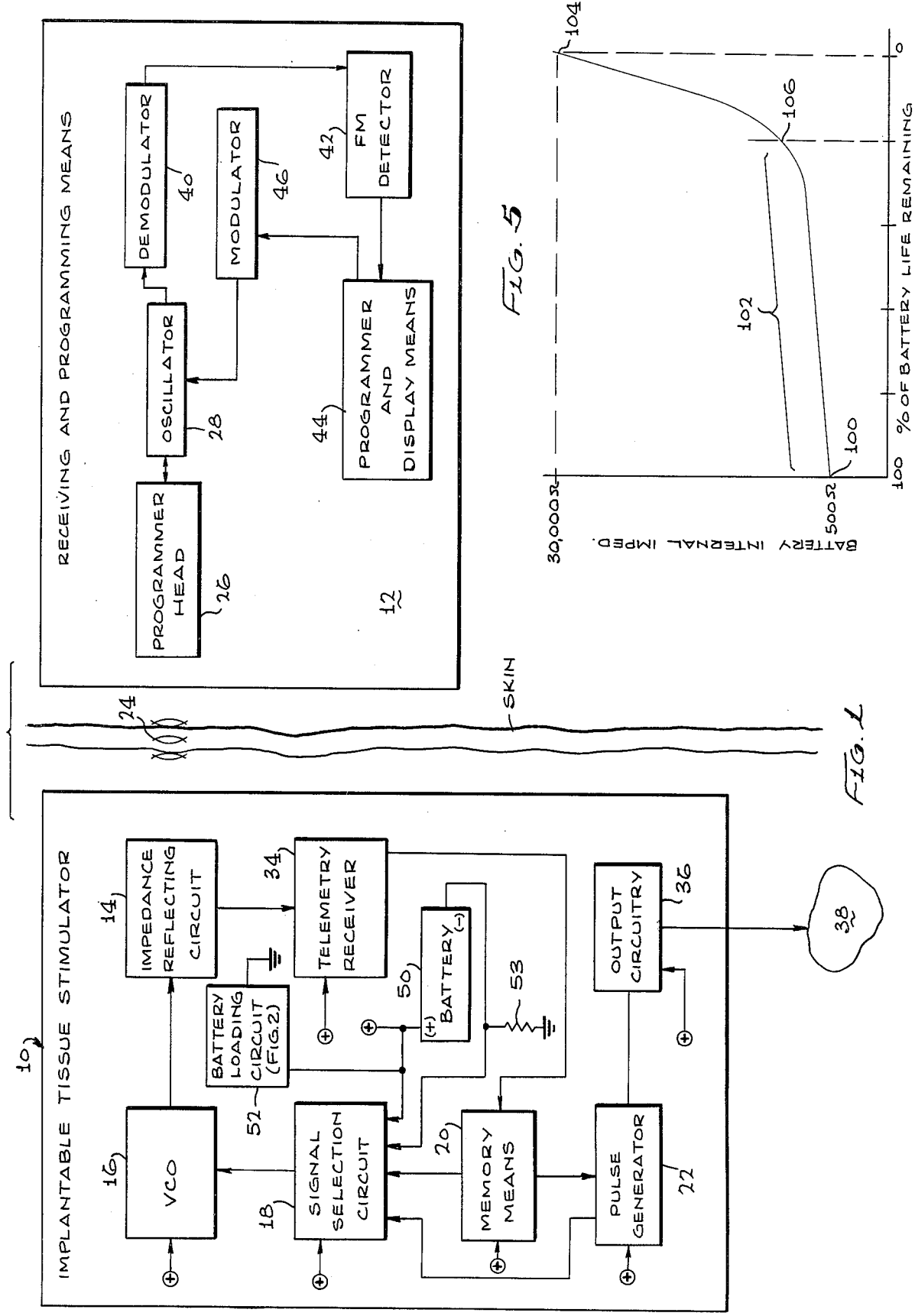
FIG. 1 is a block diagram of a implantable tissue stimulator incorporating the battery monitoring means provided by the invention.

A tissue stimulator system in the form of a heart pacemaker incorporating a battery monitoring means provided by the invention is shown in FIG. 1. Although a heart pacemaker is shown for exemplary purposes, the tissue stimulator could also be an implantable drug injector or any other implantable device affecting a user's body. The tissue stimulator system includes an implantable tissue stimulator 10 and a receiving and programming means 12. A telemetry means is included which includes an impedance reflecting circuit 14 having an impedance relating to an output voltage of a voltage controlled oscillator (VCO) 16 whose frequency is determined by an input signal to be telemetered. A signal selection circuit 18 receives input voltages from both a memory means 20 which provides digital inputs, and a pulse generator 22 which provides an analog input. The signal selection circuit 18 includes a means for selecting one of its input voltages to be telemetered, the selection being made in accordance with control signals from the memory means 20. The selected signal frequency modulates the VCO 16. The frequency modulated VCO 16 output signal then alters the impedance of the impedance reflecting circuit 14, this impedance being magnetically coupled as schematically represented at 24 to a programmer head 26 which in turn is coupled to an oscillator 28. The output of the oscillator 28 is determined by the combined impedance of the programmer head 26. Thus the oscillator 28 output is an FM modulated signal if the coupled impedance is reactive, and an AM modulated signal if the coupled impedance is resistive. In both cases the modulation on the oscillator 28 output is related to the output of the VCO 16 which is FM modulated by the signal to be telemetered.

The implantable tissue stimulator 10 also includes a telemetry receiver 34 for receiving signals from the receiving and programming means 12 and output circuitry 36 which supplies stimulating pulses to a heart 38. The output of the oscillator 28 is provided through a demodulator 40, the output which corresponds to the output of the implantable tissue stimulator VCO 16. This output is then provided to an FM detector 42 which in turn provides an output signal to a programmer in the display means 44 which is proportional to the signal provided by the signal selection circuit. Signals to be telemetered to the implantable tissue stimulator 10 are provided to a modulator 46 which modulates the oscillator 28. The output of the oscillator 28 is magnetically coupled through the programmer head 26 to the impedance reflecting circuit 14 whose output is provided to the telemetry receiver 34. In addition, the implantable tissue stimulator is powered by a battery 50 which could be of several types, two of which are a lithium iodide battery and a lithium bromide battery. The positive terminal of the battery 50 is connected to a battery loading circuit 52, to be explained in further detail below, for loading the battery during those times when the battery internal impedance is to be measured. In addition, the negative terminal of the battery 50 is provided to the signal selection circuit 18, the negative terminal being connected to ground through a shunting resistor 53. Current through the battery loading circuit 52 flows back through the shunting resistor 53 to the battery 50 negative terminal. Thus a voltage measured at the battery negative terminal is related to current through the shunting resistor 53, this current being related to the internal impedance of the battery 50 as will be explained below. Although the above description relates to a telemetry system utilizing an impedance reflecting circuit 14, the invention is in no way limited to that specific type of telemetry system and any other type of telemetry system incorporated in an implantable tissue stimulator could also be utilized.

Figure 2:
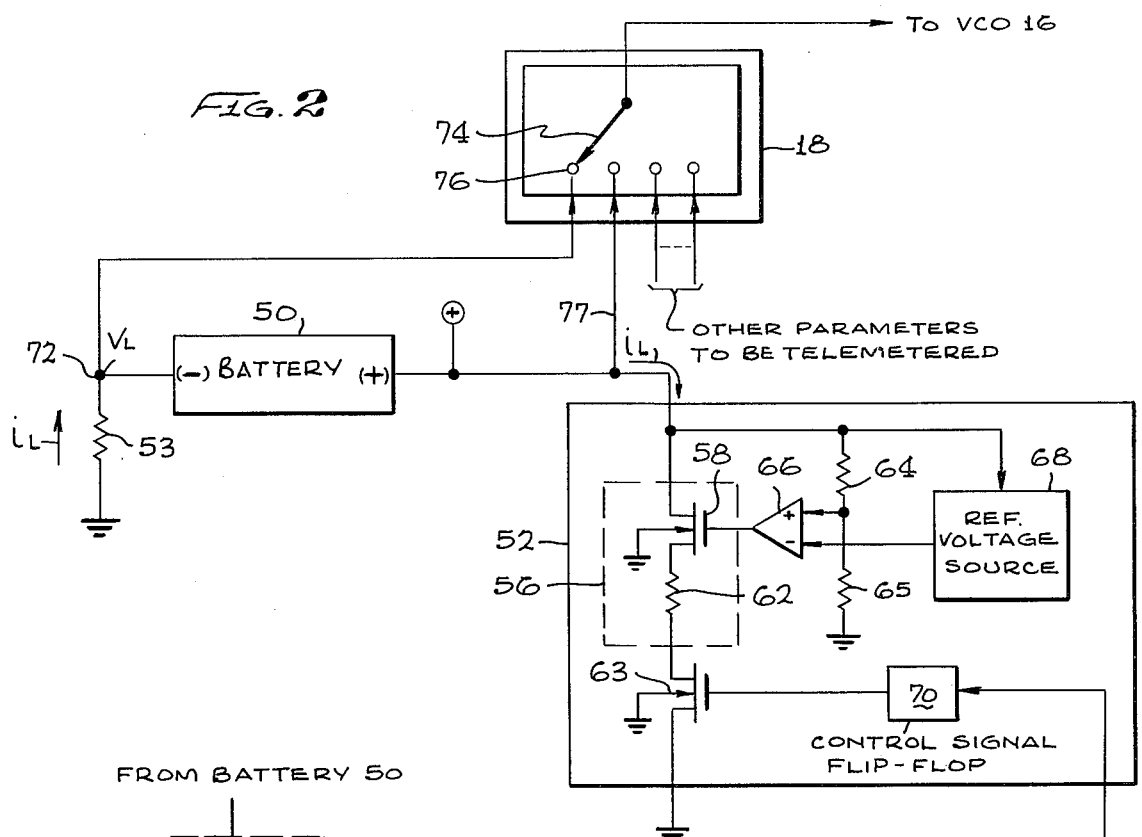
FIG. 2 is a block diagram showing one embodiment of the battery monitoring means.

As shown in FIG. 2, the battery loading circuit 52 is connected between the battery 50 positive terminal and ground. The shunting resistor 53 is connected between the battery 50 negative terminal and ground, the negative terminal also being connected to the signal selection circuit 18. The battery loading circuit includes a variable loading means 56 having a first field effect transistor (FET) 58 and a source resistor 62. A second field effect transistor 63 is provided in series between the source resistor 62 and ground. The first field effect transistor 58 is connected to the battery 50 positive terminal and through the source resistor 62 to the second field effect transistor 6. A voltage divider network is provided which includes a first resistor 64 and a second resistor 65 in series with the first resistor. The network is connected between the battery positive terminal and ground. The voltage at the connection point between the first and second resistors, 64 and 65, is referred to as a scaled battery voltage. An operational amplifier 66 has a positive input which is connected to the scaled battery voltage, and a negative input which is connected to a reference voltage source 68. The reference voltage 68 could be of several types including a Zener diode or a band gap reference voltage source. The operational amplifier 66 provides an output voltage to the control electrode of the first field effect transistor 58. This output voltage is related to the difference between the voltage of the positive terminal of the battery 50 and the output of the reference voltage source 68. The first FET 58 and the source resistor 62 form a source follower circuit such that a battery loading current I sub L is related to the output of the operational amplifier 66. Thus the battery loading current I sub L is increased until it causes the scaled battery voltage to equal that of the reference voltage source 68. The drop in battery output voltage is due to the loading current flowing through the internal impedance of the battery 50. In a specific application, the battery is a lithium iodide battery having a nominal open circuit voltage of 2.8 volts, the reference voltage source has an output voltage of 1.15 volts, and the first and second resistors 64 and 65 have the same resistance value. Thus, the current through the first field effect transistor 58 is increased in a closed-loop manner by the output of the operational amplifier 66 until the current drawn through the internal impedance of the battery causes the loaded battery voltage to drop to 2.3 volts. Of course, the reference voltage source 68 could have an output voltage greater than that of the battery 50. The output voltage could then be appropriately scaled prior to its being provided to the operational amplifier 66.

A control signal flip-flop 70 is provided, the state of the flip-flop being determined by a signal from the memory means 20. When the flip-flop 70 is in a first state, its output signal is chosen to cause the second field effect transistor 63 to be conductive; when the control flip-flop 70 is in a second state, its output signal is chosen to cause the second field effect transistor 63 to be nonconductive. Thus, during periods when it is not desired to monitor the internal impedance of the battery 50, the control signal flip-flop 70 is configured by the memory means 20 so that the second field effect transistor 63 is not conductive, thereby preventing a current drain from the battery 50 by the battery monitoring means. However, in response to an externally generated telemetry signal, the memory means 20 can be configured to cause the control signal flip-flop 70 to be in the first state, thereby making the second field effect transistor 63 conductive. The source resistor 62 also prevents the battery 50 from being shorted to ground should both the first and second transistors 58 and 63 fail in a conductive state. Thus, the loading current I sub L drawn from the battery 50 is controlled by the variable loading means 56 so that the scaled battery voltage 50 equals the output voltage of the reference voltage source 68. The loading current I sub L then flows back to the negative terminal of the battery 50 through the dropping resistor 53. Thus, the voltage V sub L at the negative terminal of the battery 50 is directly related to the value of the loading current I sub L which, as previously explained, is related to the internal impedance of the battery 50. This voltage V sub L at point 72 comprises a battery monitoring signal, and is provided to the signal selection circuit 18. The signal selection circuit 18 has a switch means 74 for connecting the battery monitoring voltage V sub L on a battery telemetry terminal 76 to the VCO 16. The switch means 74 could be any type of electronic switch such as FET switches.

The battery 50 output voltage is also provided to the signal selection circuit 18 via a battery line 77. The purpose of telemetering the battery output voltage directly is to provide a means for determining the unloaded battery voltage to solve the equation (V sub OC)−(V sub I)=(R sub B)(I sub L)

where
V sub OC=Unloaded battery output voltage
V sub I=Battery output voltage when the scaled battery voltage equals the reference voltage.
R sub B=Battery internal impedance
I sub L=Battery current when the scaled battery voltage equals the reference voltage.

When the values of V sub OC, V sub I, and I sub L are known, R sub B can be calculated. Other means for determining V sub OC include generating an alternate scaled battery voltage for the operational amplifier 66 by providing a resistor which, in response to a predetermined telemetry signal, is connected in parallel across the second resistor 65. This creates two values for V sub I, and I sub L, thereby providing two equations each having V sub OC and R sub B as unknowns. These simultaneous equations can be solved for V sub OC and R sub B. Another means would be to provide two reference voltages, which again would result in two simultaneous equations from which V sub OC and R sub B could be calculated. Also, V sub OC could be assumed to be a predetermined value.

Figure 3:
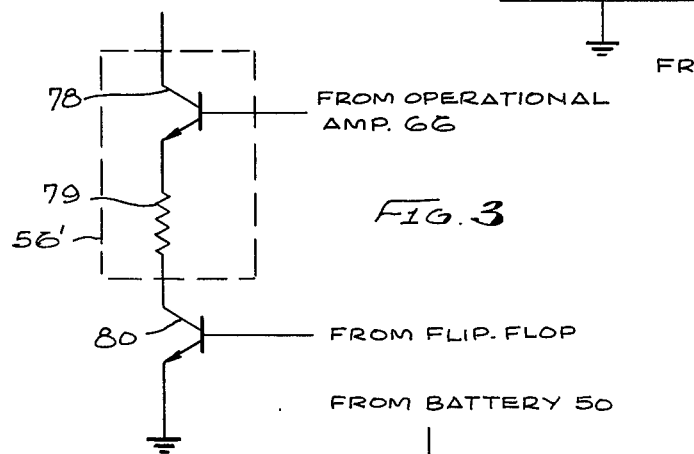
FIG. 3 is a schematic diagram showing a further embodiment of the battery monitoring means.

A further embodiment of the variable loading means 56 can be seen in FIG. 3. Here, a variable loading means 56' includes a first transistor 78 and an emitter follower resistor 79. A second transistor 80 is also provided in lieu of the second field effect transistor 63. Operation of the variable loading means 56' is the same as that described for the variable loading means 56 in conjunction with the FIG. 2 explanation.

Figure 4:
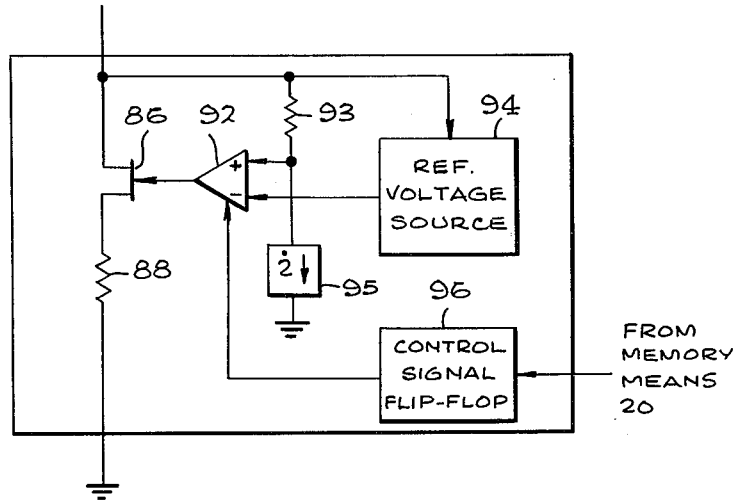
FIG. 4 is a block and schematic diagram showing a still further embodiment of the battery monitoring means provided by the invention.

Another embodiment of the invention can be seen in FIG. 4. This embodiment ncludes a field effect transistor (FET) 86 and a source resistor 88, the combination forming a source follower circuit as in the FIG. 2 embodiment. An operational amplifier 92, a voltage reference source 94 and a control signal flip-flop 96 are also provided. However, the positive input to the operational amplifier 92 is connected to the battery 50 through a scaling resistor 93 and to a constant current source 95. Thus, the input voltage to the operational amplifier is equal to the battery output voltage minus the voltage drop across the scaling resistor 93, this drop being equal to the current provided by the constant current source 94 times the value of the resistor 93. Utilizing this embodiment, it can be appreciated that the input to the operational amplifier is equal to the battery voltage minus a constant because the resistor 93 and the current provided by the constant current source 94 are constants. In operation, the battery 50 output voltage is provided directly to the reference voltage source 94, its output voltage being provided to the minus input of the operational amplifier 92. The operational amplifier 92 is chosen to be responsive to the state of an output signal of the flip-flop 96 which is controlled by a signal from the memory means 20. Thus, in accordance with a signal from the memory means 20, the operational amplifier 92 can either be activated or deactivated. When the operational amplifier is deactivated, its output signal to the control electrode of the FET 86 is chosen to render it non-conductive. When the signal from the flip-flop 96 allows the operational amplifier 92 to operate normally, then its output signal controls the FET 86.

Utilization of the battery loading circuit described above can be seen in reference to FIG. 5. However, it should be remembered that FIG. 5 is only a qualitative representation and the internal impedance shown do not refer to any particular battery type. Referring now to FIG. 5, a fully charged battery may have an internal impedance of 500 ohms as shown at 100. During the first 80% of battery life, the increase in internal impedance is substantially linear as shown at 102. However, when only 20% of the original battery life is remaining, the internal impedance increases significantly and becomes very high as shown at 104. Calculations of battery internal impedance from telemetered battery monitoring signals generated as above described provides a means for determining the life remaining in an implanted battery. The battery should be replaced as soon as the internal impedance begins to rise rapidly as can be seen at 106.

It should now be apparent that a battery monitoring means has been described in which a battery is loaded by a closed loop servo system wherein the voltage drop resulting from current flowing through the battery internal impedance lowers the battery output voltage to a value having a predetermined relationship with respect to a reference voltage. The current flowing through the battery is then determined, and a battery monitoring signal in response thereto is generated. This signal is telemetered to an external receiving means.

What is claimed is:

1. In an implantable tissue stimulator powered by a battery having a positive terminal and a negative terminal, a battery monitoring means comprising:
   means for drawing a loading current from said battery that results in said battery output voltage having a predetermined relationship with respect to a reference voltage; and
   means for generating a battery monitoring signal related to said loading current, said battery monitoring signal being related to the internal impedance of said battery.

2. The battery monitoring means of claim 1 wherein said implantable tissue stimulator comprises a telemetry means for transmitting and receiving signals related to the operation of said tissue stimulator, said battery monitoring means further comprising means for providing said battery monitoring signal to said telemetry means.

3. The battery monitoring means of claim 2 wherein said means for drawing comprises:
a variable loading means between said battery positive and negative terminals
means for controlling said variable loading means until said battery output voltage has said predetermined relationship with respect to said reference voltage.

4. The battery monitoring means of claim 3 wherein said variable loading means comprises a transistor.

5. The battery monitoring means of claim 4 wherein said transistor comprises a field effect transistor (FET).

6. The battery monitoring means of claim 3 wherein said means for controlling comprises an operational amplifier having a first input comprising said reference voltage and a second input comprising a voltage related to said battery output voltage, and an output voltage related to a difference between said first and second input voltages, said operational amplifier output voltage controlling said variable loading means until said operational amplifier first and second inputs have a predetermined relationship with respect to each other.

7. The battery monitoring means of claim 6 wherein said variable loading means comprises a first transistor and said battery monitoring means further comprises means responsive to said telemetry means for preventing current from flowing through said first transistor.

8. The battery monitoring means of claim 7 wherein said means responsive to said telemetry means comprises a second transistor in series with said first transistor.

9. The battery monitoring means of claim 6 wherein said operational amplifier comprises a third input responsive to a predetermined biasing voltage for causing said operational amplifier output voltage to provide an output signal that causes said variable loading means to be non-conductive, said means responsive to said telemetry means comprising:
means for generating said biasing voltage; and
means for providing said biasing voltage to said operational amplifier third input.

10. The battery monitoring means of claim 1 wherein said means for drawing is connected to one terminal of said battery, said means for generating comprises:
a shunting resistor connected to the other terminal of said battery so that said loading current flows through said shunting resistor; and
means for generating a signal related to the voltage drop across said shunting resistor, said signal comprising said battery monitoring signal.

11. In an implantable tissue stimulator powered by a battery having positive and negative terminals, said tissue stimulator having a telemetry means for transmitting and receiving signals related to the operation of said tissue stimulator, a battery monitoring means comprising:
a variable loading means connected to a first of said battery terminals;
means for generating a reference voltage;
means for controlling said variable loading means so that a voltage related to said battery output voltage has a predetermined relationship with respect to said reference voltage, said battery providing a loading current when said predetermined relationship exists;
means for generating a battery monitoring signal related to said loading current, said battery monitoring signal being related to said battery internal impedance; and
means for providing said battery monitoring signal to said telemetry means.

12. The battery monitoring means of claim 11 wherein said variable loading means comprises a loading transistor.

13. The battery monitoring means of claim 12 wherein said means for altering comprising:
an operational amplifier having said voltage related to said battery output voltage as a first input, said reference voltage as a second input, and an output voltage related to a difference between said first and second input voltages; and
means for connecting said operational amplifier output voltage to a control electrode of said loading transistor, thereby altering current through said battery until said operational amplifier first and second inputs have a predetermined relationship with respect to each other.

14. The battery monitoring means of claim 13 wherein said variable loading means further comprises an impedance in series with said loading transistor.

15. The battery monitoring means of claim 14 wherein said loading transistor is a field effect transistor (FET).

16. The battery monitoring means of claim 15 further comprising:
a blocking transistor in series with said loading transistor; and
means responsive to said telemetry means for causing said blocking transistor to be non-conductive.

17. The battery monitoring means of claim 15 further comprising means responsive to said telemetry system for causing said operational amplifier to provide an output signal that causes said loading transistor to be non-conductive.

18. The battery monitoring means of claim 11 wherein said means for generating a battery monitoring signal comprises:
a shunting resistor connected to a second of said battery output terminals so that said loading current flows through said shunting resistor; and
means for generating a signal related to a voltage drop across said shunting resistor as said loading current flows therethrough, said signal comprising said battery monitoring signal.

19. In an implantable tissue stimulator powered by a battery, a method for determining the internal impedance of said battery comprising the steps of:
drawing a loading current from said battery that results in said battery output voltage having a predetermined relationship with respect to a reference voltage, said loading current being related to the internal impedance of said battery; and
generating a battery monitoring signal related to said loading current.

20. The method of claim 19 wherein said implantable tissue stimulator comprises a telemetry means for transmitting and receiving signals related to the operation of said tissue stimulator, said method further comprising the step of providing said battery monitoring signal to said telemetry means.

* * * * *